United States Patent [19]
De Lucchi et al.

[11] Patent Number: 4,777,274
[45] Date of Patent: Oct. 11, 1988

[54] PROCESS FOR THE SELECTIVE PREPARATION OF ISOSORBIDE-2-MONONITRATE FROM ISOSORBIDE-2,5-DINITRATE

[75] Inventors: Ottorino De Lucchi; Fabiola Filipuzzi; Giorgio Modena, all of Padua; Ettore Camera, Gorizia, all of Italy

[73] Assignee: Consiglio Nazionale Delle Ricerche - Dinamite Spa, Udine, Italy

[21] Appl. No.: 928,039

[22] Filed: Nov. 7, 1986

[51] Int. Cl.$^4$ .................................... C07D 493/04
[52] U.S. Cl. ..................................... 549/464
[58] Field of Search ........................ 549/347, 464

[56] References Cited

U.S. PATENT DOCUMENTS 4,381,400  4/1983  Emeury et al. .............. 549/464
4,713,466 12/1987  De Lucchi et al. ......... 549/464

OTHER PUBLICATIONS

Moraghan et al., Chemical Abstracts 86:188400h.

*Primary Examiner*—Norma S. Milestone
*Attorney, Agent, or Firm*—Parkhurst, Oliff & Berridge

[57] ABSTRACT

A process for the preparation of isosorbide-2-mononitrate (I)

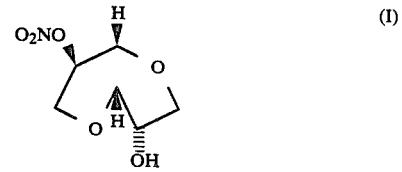

from isosorbide-2,5-dinitrate (II)

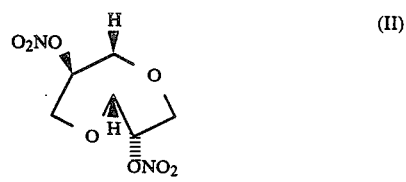

The isosorbide-2,5-dinitrate (II) is treated, in a reaction medium consisting of an aqueous organic solvent, with salts of metals of low oxidation state.

Isosorbide-2-mononitrate (I) is obtained with high selectivity.

6 Claims, No Drawings

PROCESS FOR THE SELECTIVE PREPARATION OF ISOSORBIDE-2-MONONITRATE FROM ISOSORBIDE-2,5-DINITRATE

This invention relates to a new process for the preparation of isosorbide-2-mononitrate (I):

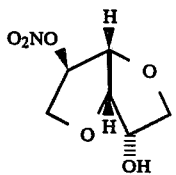

More particularly, the invention relates to a process for the selective preparation of isosorbide-2-mononitrate (I) from isosorbide-2,5-dinitrate (II):

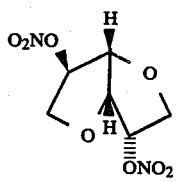

Isosorbide-2-mononitrate (I) is of considerable pharmaceutical importance in that it acts as a non-specific smooth muscle relaxant, and particularly as a coronary vasodilator (J. Pharmacol. Exp. Ther., 180, 732–742, 1972; Nuov. Presse Med., Tile 9, 2424–2427, 1980).

Isosorbide-5-mononitrate (III)

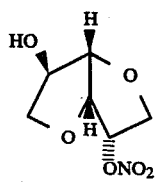

also presents analogous interesting characterstics from the pharmacological viewpoint. However, whereas for compound (I) the half-life is 1.8 hours, for compound (III) the half-life is 4.2 hours.

Because of this fundamental difference in the pharmaceutical application of the two compounds, it is necessary when preparing them from isosorbide-2,5-dinitrate (II) to operate in such a manner as to selectively obtain the one or other of the two isomers (I) and (III).

Some processes are known for preparing isosorbide mononitrate.

However, only one process for the selective preparation of isosorbide-2-mononitrate (I) is known (German Pat. No. 2,903,983). In this process, tetrabutylammonium nitrite and isomannide-2-triflate are used as reagents, these being of laborious preparation and hgh cost. This is therefore a process which is not suitable for industrial application.

Other known processes for preparing isosorbide-2-mononitrate use isosorbide-2,5-dinitrate (II) as their starting substance, but these are non-selective processes, such as the process described in French Pat. No. 8,103,906, in which isosorbide-2,5-dinitrate (II) is treated with hydrazine hydrate to obtain a mixture of the two isomers (I) and (III). This process also has the drawbacks of operating with a reagent which is a known carcinogen, namely hydrazine hydrate, and of being of low yield. We have now discovered a new process for the preparation of isosorbide-2-mononitrate (I) from isosorbide-2,5-dinitrate, which compared with known processes has remarkable advantages, including:
the use of easily obtainable low-cost reagents;
easily attainable operating conditions;
high selectivity and high yield of the required product;
ease of application to industrial production.

The process for the preparation of isosorbide-2-mononitrate according to the invention is characterised in that isosorbide-2,5-dinitrate is treated, in a reaction medium consisting of an organic solvent and water, with salts of metals of low oxidation state, to obtain isosorbide-2-mononitrate (I) with high selectivity.

These and further characterstics and advantages of the process according to the present invention will be more apparent from the non-limiting description of preferred methods of implementing the process, given hereinafter for illustrative purposes.

The reaction medium preferably consists of ethyl alcohol and water in a volume ratio of between 50/50 and 80/20, but other organic solvents can be used instead of the ethyl alcohol, such as methyl alcohol, propyl alcohol, acetonitrile, acetic acid, ethylene glycol, dioxane, tetrahydrofuran etc.

The inorganic compounds preferably used are ferrous sulphate and cuprous chloride. However, use can also be made of other saline compounds of Cu(I) and Fe(II), or of other metals such as Co(II), Cr(II), Mn(II), Pb(II) and Sn(II), and in general salts of metal ions which can act as reducing agents thus attaining higher oxidation states.

The isosorbide-2,5-dinitrate is dissolved in the reaction medium under agitation at ambient temperature, and the salt is then added under agitation.

The temperature is brought to between 0° C. and the boiling point of the mixture under reflux, and the reaction is continued under agitation for a time of between 2 and 48 hours.

The ratio of moles of isosorbide-2,5-dinitrate to gram equivalents of reducing ions used for the reaction is preferably between 1 and 10.

On termination of the reaction, the suspension obtained is cooled and then filtered. The solution is evaporated to dryness under vacuum, and the residue dissolved in a small quantity of $CH_2Cl_2$. If necessary, any insoluble residues are filtered off, after which a seeding crystal of isosorbide-2-mononitrate is added to the solution to crystallise the product isosorbide-2-mononitrate with high purity.

If unreacted isosorbide-2,5-dinitrate is present in the reaction mixture after the preparation, it can be easily recycled to the next preparation.

The following examples are given as non-limiting illustration of the characteristics of the process according to the invention.

EXAMPLE 1

50 ml of an aqueous ethanol solution with an ethanol/water volume ratio of 70/30 are fed into a 100 ml laboratory flask fitted with a thermometer and agitator. 1 g (4.2 mmoles) of isosorbide-2,5-dinitrate is then added and is dissolved under agitation. Finally, 6 g (21.6 mmoles) of $FeSO_4.7H_2O$ heptahydrate are added. The mixture is heated and kept boiling under reflux for 24 hours under agitation. On termination of the reaction, the suspension obtained is cooled to 20° C. and filtered. The solution is evaporated under vacuum and 2 ml of CH$_2$Cl$_2$ are then added. A seeding crystal of isosorbide-2-mononitrate is then added to crystallise 0.65 g (3.4 mmoles) of isosorbide-2-mononitrate (yield 81%) which on GLC analysis is found to be of 98% purity. M.P.=55° C. (53° C. in the literature).

EXAMPLE 2

10 ml of an aqueous ethanol solution with an ethanol/water volume ratio of 70/30 are fed into a laboratory flask as in Example 1. 1 g (4.2 mmoles) of isosorbide-2,5-dinitrate is then added and is dissolved under agitation. Finally, 3 g (30 mmoles) of cuprous chloride are added. The mixture is heated and kept boiling under reflux for 12 hours under agitation. After this reaction time, the mixture is analysed by gas chromatography and the following results are found: isosorbide 15%, isosorbide-2-nitrate 45%, isosorbide-5-nitrate 6.8% and unreacted isosorbide-2,5-dinitrate 33.2%.

We claim:

1. A selective process for the preparation of isosorbide-2-mononitrate

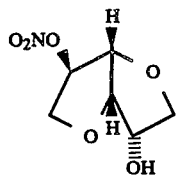
(I)

from isosorbide-2,5-dinitrate

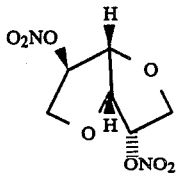
(II)

characterized in that the isosorbide-2,5-dinitrate (II) is treated, in a reaction medium consisting of a mixture of a water miscible organic solvent and water in a volume ratio between 50/50 and 80/20, with metallic salts of low oxidation state selected from the group consisting of Cu(I), Fe(II), Co(II), Cr(II), Mn(II), Pb(II) and Sn(II) in a ratio of equivalents of metallic salt to moles of isosorbide-2,5-dinitrate between 10:1 and 1:1, the reaction being carried out at reflux temperatures.

2. A process as claimed in claim 1, wherein the water miscible organic solvent is selected from the group consisting of ethyl alcohol, methyl alcohol, propyl alcohol, acetonitrile, acetic acid, ethylene glycol, dioxane and tetrahydrofuran.

3. A process as claimed in claim 1, wherein said organic solvent is not subject to reduction.

4. A process as claimed in claim 1, wherein said metallic salts are salts of Fe(II) or of Cu(I).

5. A process as claimed in claim 1, wherein said treatment of isosorbide-2,5-dinitrate is carried out under agitation.

6. A process as claimed in claim 1, wherein said treatment of isosorbide-2,5-dinitrate is carried out for a time of between 2 and 48 hours.

* * * * *